United States Patent
Sachanandani et al.

(10) Patent No.: US 9,037,222 B2
(45) Date of Patent: *May 19, 2015

(54) DIFFERENTIATING DECOMPENSATION DETECTION BASED ON CO-MORBIDITIES IN HEART FAILURE

(71) Applicant: Cardiac Pacemakers, Inc., St. Paul, MN (US)

(72) Inventors: Haresh G. Sachanandani, Culver City, CA (US); Yunlong Zhang, Mounds View, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 16 days.

This patent is subject to a terminal disclaimer.

(21) Appl. No.: 14/140,710

(22) Filed: Dec. 26, 2013

(65) Prior Publication Data

US 2014/0107503 A1 Apr. 17, 2014

Related U.S. Application Data

(63) Continuation of application No. 13/848,869, filed on Mar. 22, 2013, now Pat. No. 8,644,916, which is a continuation of application No. 12/249,817, filed on Oct. 10, 2008, now Pat. No. 8,417,325.

(60) Provisional application No. 60/979,749, filed on Oct. 12, 2007.

(51) Int. Cl.
*A61B 5/0205* (2006.01)
*A61B 5/021* (2006.01)
(Continued)

(52) U.S. Cl.
CPC ........... *A61B 5/0205* (2013.01); *A61B 5/02455* (2013.01); *A61B 5/042* (2013.01);
(Continued)

(58) Field of Classification Search
CPC .... A61B 5/042; A61B 5/7275; A61B 5/0205; A61B 5/7282; A61B 5/7264; A61B 5/686; A61B 5/1118; A61B 7/02; A61B 5/029; A61B 5/021; A61B 5/02028; A61B 5/0002; A61B 5/0538; A61B 5/145; A61B 5/14532; A61B 5/02455; A61B 5/08; A61N 1/3956; A61N 1/3627
USPC ......................................................... 600/513
See application file for complete search history.

(56) References Cited

U.S. PATENT DOCUMENTS 4,686,987 A 8/1987 Salo et al.
6,076,015 A 6/2000 Hartley et al.
(Continued)

FOREIGN PATENT DOCUMENTS

EP 1582233 A2 10/2008
EP 2219518 B1 8/2012
(Continued)

OTHER PUBLICATIONS

"U.S. Appl. No. 12/249,817, Non Final Office Action mailed Aug. 23, 2012", 5 pgs.
(Continued)

*Primary Examiner* — Mark W Bockelman
(74) *Attorney, Agent, or Firm* — Schwegman Lundberg & Woessner, P.A.

(57) ABSTRACT

This document discusses, among other things, a system comprising a sensor signal processor configured to receive a plurality of electrical sensor signals produced by a plurality of sensors and at least one sensor signal produced by an implantable sensor, a memory that includes information indicating a co-morbidity of a subject, a sensor signal selection circuit that selects a sensor signal to monitor from among the plurality of sensor signals, according to an indicated co-morbidity, a threshold adjustment circuit that adjusts a detection threshold of the selected sensor signal according to the indicated co-morbidity, and a decision circuit that applies the adjusted detection threshold to the selected sensor signal to determine whether an event associated with worsening heart failure (HF) occurred in the subject and outputs an indication of whether the event associated with worsening HF occurred to a user or process.

20 Claims, 7 Drawing Sheets

(51) Int. Cl.
*A61B 5/02* (2006.01)
*A61B 5/029* (2006.01)
*A61B 5/00* (2006.01)
*A61B 5/11* (2006.01)
*A61B 7/02* (2006.01)
*A61B 5/042* (2006.01)
*A61N 1/39* (2006.01)
*A61B 5/0245* (2006.01)
*A61B 5/08* (2006.01)
*A61B 5/145* (2006.01)
*A61N 1/362* (2006.01)
*A61B 5/053* (2006.01)

(52) U.S. Cl.
CPC . *A61B 5/08* (2013.01); *A61B 5/145* (2013.01); *A61B 5/14532* (2013.01); *A61B 5/7275* (2013.01); *A61N 1/3627* (2013.01); *A61N 1/3956* (2013.01); *A61B 5/0002* (2013.01); *A61B 5/02028* (2013.01); *A61B 5/021* (2013.01); *A61B 5/029* (2013.01); *A61B 5/0538* (2013.01); *A61B 5/1118* (2013.01); *A61B 5/686* (2013.01); *A61B 5/7264* (2013.01); *A61B 5/7282* (2013.01); *A61B 7/02* (2013.01)

(56) References Cited

U.S. PATENT DOCUMENTS

| | | | |
|---|---|---|---|
| 6,666,826 B2 | 12/2003 | Salo et al. | |
| 7,248,919 B2 | 7/2007 | Carlson et al. | |
| 8,417,325 B2 | 4/2013 | Sachanandani et al. | |
| 8,644,916 B2 * | 2/2014 | Sachanandani et al. | 600/513 |
| 2005/0197674 A1 | 9/2005 | McCabe et al. | |
| 2006/0010090 A1 | 1/2006 | Brockway et al. | |
| 2006/0282000 A1 | 12/2006 | Zhang et al. | |
| 2007/0249950 A1 | 10/2007 | Piaget et al. | |
| 2007/0270675 A1 | 11/2007 | Kane et al. | |
| 2008/0177156 A1 | 7/2008 | Zhang et al. | |
| 2009/0099426 A1 | 4/2009 | Sachanandani et al. | |
| 2013/0211266 A1 | 8/2013 | Sachanandani et al. | |

FOREIGN PATENT DOCUMENTS

| | | |
|---|---|---|
| JP | 5119334 | 10/2012 |
| WO | WO-2006127594 A2 | 11/2006 |
| WO | WO-2007064682 A1 | 6/2007 |
| WO | WO-2009051658 A1 | 4/2009 |

OTHER PUBLICATIONS

"U.S. Appl. No. 12/249,817, Notice of Allowance mailed Dec. 10, 2012", 5 pgs.

"U.S. Appl. No. 12/249,817, Response filed Nov. 21, 2012 to Non Final Office Action mailed Aug. 23, 2012", 11 pgs.

"U.S. Appl. No. 13/848,869, Non Final Office Action mailed Jun. 21, 2013", 6 pgs.

"U.S. Appl. No. 13/848,869, Notice of Allowance mailed Sep. 25, 2013", 6 pgs.

"U.S. Appl. No. 13/848,869, Response filed Aug. 23, 2013 to Non Final Office Action mailed Jun. 21, 2013", 8 pgs.

"International Application Serial No. PCT/US2008/011643, International Search Report mailed Feb. 12, 2009", 4 pgs.

"International Application Serial No. PCT/US2008/011643, Written Opinion mailed Feb. 12, 2009", 8 pgs.

"Japanese Application Serial No. 2010-528891, Office Action mailed Aug. 14, 2012", 6 pgs.

"Japanese Application Serial No. 2010-528891, Response filed Sep. 12, 2012 to Office Action mailed Aug. 14, 2012", (w/ English Translation), 9 pgs.

Burger, A. J., et al., "Effect of diabetes Mellitus on Heart Rate Variability in Patients with Congestive Heart Failure", Journal of Pacing and Clinical Electrophysiology vol. 24(1), (Jan. 2001), 53-59.

Kaplan, et al., "Comparison of CRT-D Device Diagnostics in HF Patients With and Without Diabetes Mellitus", Journal of Cardial Failure, Churchill Livingstone, Naperville, IL vol. 13(6), (Aug. 1, 2007), S127.

* cited by examiner

DIFFERENTIATING DECOMPENSATION DETECTION BASED ON CO-MORBIDITIES IN HEART FAILURE

RELATED APPLICATIONS

This application is a continuation of U.S. patent application Ser. No. 13/848,869, filed Mar. 22, 2013, now issued as U.S. Pat. No. 8,644,916, which is a continuation of U.S. patent application Ser. No. 12/249,817, now U.S. Pat. No. 8,417,325, filed Oct. 10, 2008, which claims the benefit under 35 U.S.C. §119(e) of U.S. Provisional Patent Application Ser. No. 60/979,749, filed on Oct. 12, 2007, each of which is incorporated herein by reference in its entirety.

BACKGROUND

Implantable medical devices (IMDs) include devices designed to be implanted into a patient. Some examples of these devices include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. Some IMDs derive measurements of hemodynamic parameters related to chamber filling and contractions from electrical signals provided by sensors. Sometimes patients who receive IMDs have experienced heart failure (HF) decompensation or other events associated with worsening HF. Some patients have experienced repeated HF decompensations. Symptoms associated with worsening HF include pulmonary and/or peripheral edema, dilated cardiomyapathy, or ventricular dilation. Early attention to signs and symptoms of HF decompensation is needed for the health of the patient and allows early initiation of treatment.

OVERVIEW

This document relates generally to systems, devices, and methods for monitoring hemodynamic parameters of a patient or subject. A system example includes a sensor signal processor configured to receive a plurality of electrical sensor signals produced by a plurality of sensors and at least one sensor signal produced by an implantable sensor, a memory including information indicating a co-morbidity of a subject, a sensor signal selection circuit configured to select a sensor signal to monitor from among the plurality of sensor signals, according to an indicated co-morbidity, a threshold adjustment circuit configured to adjust a detection threshold of the selected sensor signal according to the indicated co-morbidity, and a decision circuit configured to apply the adjusted detection threshold to the selected sensor signal to determine whether an event associated with worsening HF occurred in the subject and to output an indication of whether the event associated with worsening HF occurred to a user or process.

A method example includes receiving a plurality of sensor signals, each of which include physiologic information and at least one sensor signal provided by an implantable sensor, selecting at least one sensor signal to monitor according to a co-morbidity of a subject indicated in stored co-morbidity information, manually and/or automatically adjusting a detection threshold of the selected sensor signal according to the indicated co-morbidity, applying the detection threshold to the selected sensor signal to determine whether an event associated with worsening HF occurred, and providing an indication of whether the event associated with worsening HF occurred to a user or process.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

Figure 1:
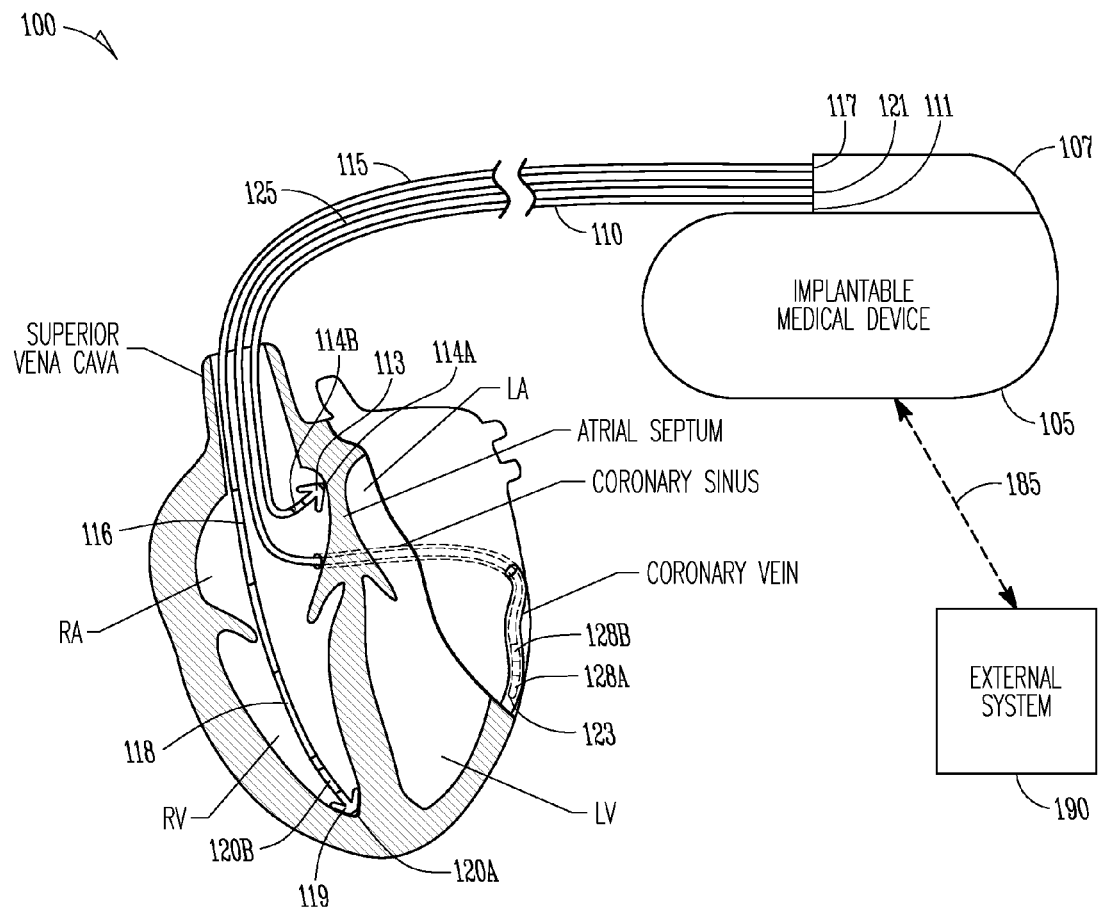
FIG. 1 is an illustration of portions of a system that uses an IMD.

FIG. 1 is an illustration of portions of a system 100 that uses an IMD 105. Examples of IMD 105 include, without limitation, a pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." The system 100 also typically includes an IMD programmer or other external system 190 that communicates one or more wireless signals 185 with the IMD 105, such as by using radio frequency (RF) or by one or more other telemetry methods.

The example shown includes right atrial (RA) lead 110 having a proximal end 111 and a distal end 113. The proximal end 111 is coupled to a header connector 107 of the IMD 105. The distal end 113 is configured for placement in the RA in or near the atrial septum. The RA lead 110 may include a pair of bipolar electrodes, such as an RA tip electrode 114A and an RA ring electrode 114B. The RA electrodes 114A and 114B are incorporated into the lead body at distal end 113 for placement in or near the RA, and are each electrically coupled to IMD 105 through a conductor extending within the lead body. The RA lead is shown placed in the atrial septum, but the RA lead may be placed in or near the atrial appendage, the atrial free wall, or elsewhere.

The example shown also includes a right ventricular (RV) lead 115 having a proximal end 117 and a distal end 119. The proximal end 117 is coupled to a header connector 107. The distal end 119 is configured for placement in the RV. The RV lead 115 may include one or more of a proximal defibrillation electrode 116, a distal defibrillation electrode 118, an RV tip electrode 120A, and an RV ring electrode 120B. The defibrillation electrode 116 is generally incorporated into the lead body such as in a location suitable for supraventricular placement in the RA and/or the superior vena cava. The defibrillation electrode 118 is incorporated into the lead body near the distal end 119 such as for placement in the RV. The RV electrodes 120A and 120B may form a bipolar electrode pair and are generally incorporated into the lead body at distal end 119. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart.

The RV tip electrode 120A, RV ring electrode 120B, or an electrode formed on the can of IMD 105 allow for sensing an RV electrogram signal representative of RV depolarizations and delivering RV pacing pulses. In some examples, the IMD includes a sense amplifier circuit to provide amplification and/or filtering of the sensed signal. RA tip electrode 114A, RA ring electrode 114B, or an electrode formed on the can of IMD 105 allow for sensing an RA electrogram signal representative of RA depolarizations and allow for delivering RA pacing pulses. Sensing and pacing allows the IMD 105 to adjust timing of the heart chamber contractions. In some examples, the IMD 105 can adjust the timing of ventricular depolarizations with respect to the timing of atrial depolarizations by sensing electrical signals in the RA and pacing the RV at the desired atrial-ventricular (AV) delay time.

A left ventricular (LV) lead 125 can include a coronary pacing or sensing lead that includes an elongate lead body having a proximal end 121 and a distal end 123. The proximal end 121 is coupled to a header connector 107. A distal end 123 is configured for placement or insertion in the coronary vein. The LV lead 125 may include an LV ring or tip electrode 128A and an LV ring electrode 128B. The distal portion of the LV lead 125 is configured for placement in the coronary sinus and coronary vein such that the LV electrodes 128A and 128B are placed in the coronary vein. The LV electrodes 128A and 128B may form a bipolar electrode pair and are typically incorporated into the lead body at distal end 123. Each can be electrically coupled to IMD 105 such as through one or more conductors extending within the lead body. LV tip electrode 128A, LV ring electrode 128B, or an electrode formed on the can of the IMD 105 allow for sensing an LV electrogram signal representative of LV depolarizations and delivering LV pacing pulses.

The IMDs may be configured with a variety of electrode arrangements, including transvenous, epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Some IMDs are able to sense signals representative of cardiac depolarizations using electrodes without leads.

Figure 2A:
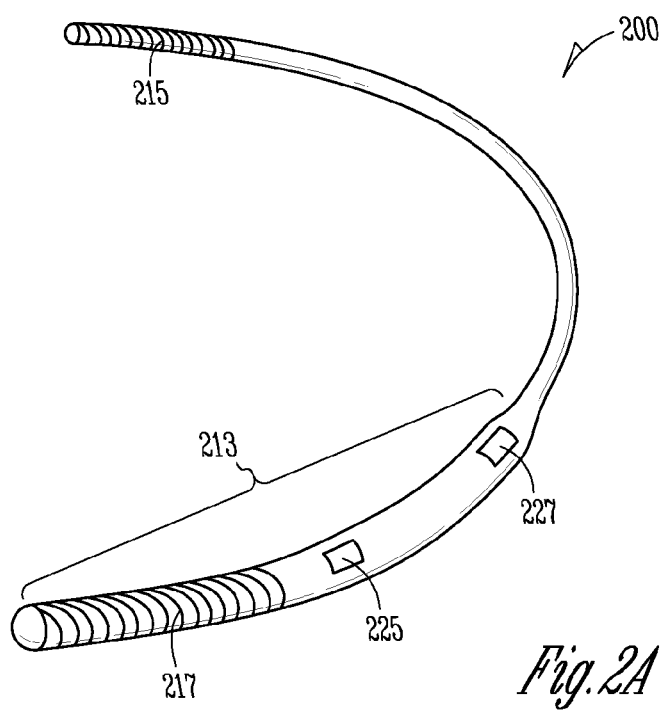
FIGS. 2A-B show an example of an IMD that does not use intravascular leads to sense cardiac signals.
Figure 2B:
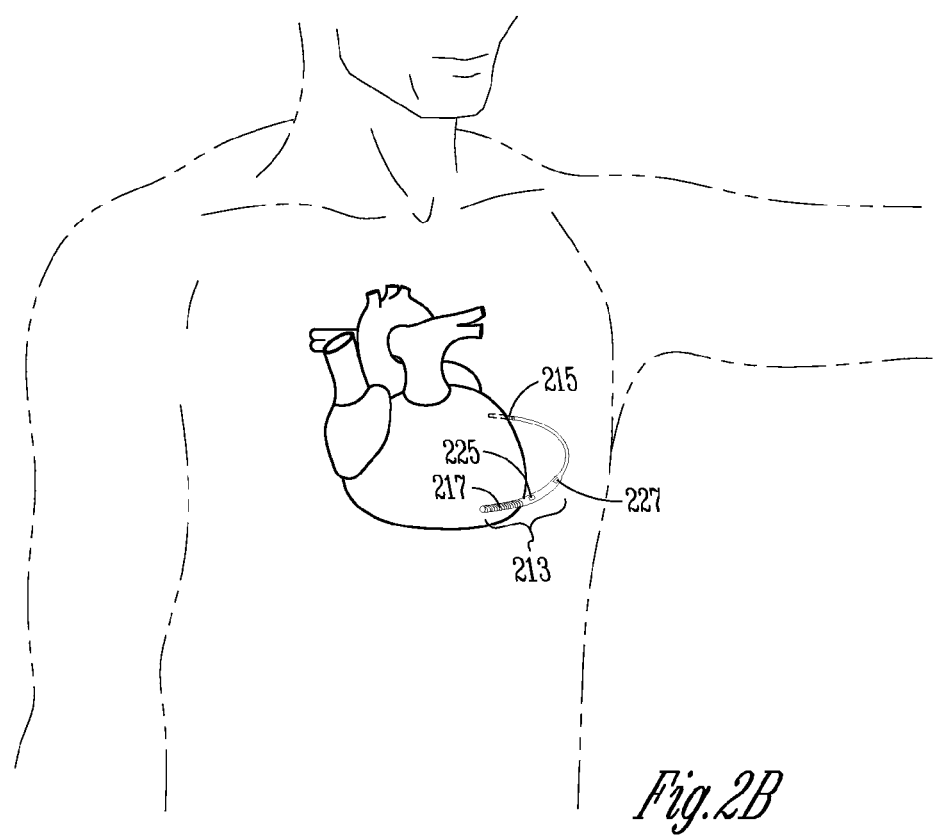

FIGS. 2A-B show an example of an IMD 200 that does not use intravascular leads to sense cardiac signals. FIG. 2A shows that the IMD 200 includes a thicker end 213 to hold the power source and circuits. The IMD 200 also includes electrodes 225 and 227 for remote sensing of cardiac signals. Cardioversion and/or defibrillation are provided through electrodes 215 and 217. FIG. 2B shows an example of the position of the IMD 200 within a patient.

Monitoring of electrical signals related to cardiac activity may provide early detection of a heart failure (HF) decompensation event or other event associated with HF. HF patients also may have different co-morbidities. Examples of co-morbidities include diabetes (DM), hypertension (HTN), apnea, myocardial infarction (MI), and chronic obstructive pulmonary disorder (COPD). An HF patient without a co-morbidity may exhibit HF differently than a patient with a co-morbidity. Also, an HF patient with a co-morbidity (e.g., diabetes) may exhibit HF differently than a patient with multiple co-morbidities (e.g., diabetes and hypertension).

Certain measurements related to hemodynamic performance can be derived from electrical signals provided by sensors. An example of such a measurement is heart rate variability (HRV) derived from intrinsic signals sensed using a cardiac signal sensing circuit. HRV can be presented as a standard deviation of sequential mean R-R intervals (SDANN), a measure of minimum heart rate, a measure of maximum heart rate, and a heart rate mean.

Differences in HF decompensation for patients will be reflected in differences in the measurements. Differences may also be evident in a patient activity log or a footprint histogram. Therefore, detection criteria for monitoring different measurements for evidence of worsening HF may be different for patients with different co-morbidities. These differences will also be reflected in the HF diagnostics recorded by IMDs.

Figure 3A:
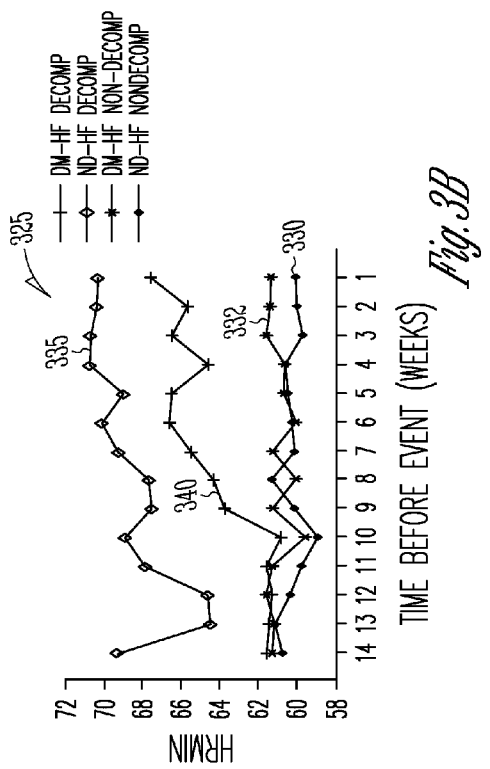
FIGS. 3A-3D show graphs of example measurements taken from subjects experiencing HF leading up to the subjects undergoing HF decompensation.

FIGS. 3A-3D show graphs of example measurements taken from subjects experiencing HF leading up to the subjects undergoing HF decompensation. FIG. 3A shows graphs 305 of measurements of an activity log versus time (in weeks) for subjects taken during a period before a HF decompensation event (at time=0). Graph 310 includes measurements of activity for subjects that experienced HF, did not undergo decompensation during the period, and were non-diabetic. Graph 312 includes activity for subjects that experienced HF, did not undergo decompensation during the period, and were diabetic. Graph 315 includes activity for subjects that experienced HF, underwent decompensation, and were non-diabetic. Graph 320 includes activity for subjects that experienced HF, underwent decompensation, and were diabetic.

The graphs 305 show that there is a difference in activity during the period between subjects that did undergo HF decompensation and those that did not undergo decompensation during the period. Thus monitoring activity such as by an activity log may help anticipate HF decompensation in subjects with HF. The graphs 305 also show that, for subjects that experienced HF decompensation, there is a difference in activity level between subjects that have a co-morbidity of diabetes and subjects that don't have diabetes. The graphs 305 further show that there is a difference in the slope of the activity levels between subjects having a co-morbidity of diabetes and subjects that don't have diabetes. Therefore, a small decrease in activity may have more significance as an indicator of an HF event for a patient with diabetes than for a patient without diabetes.

Figure 3B:
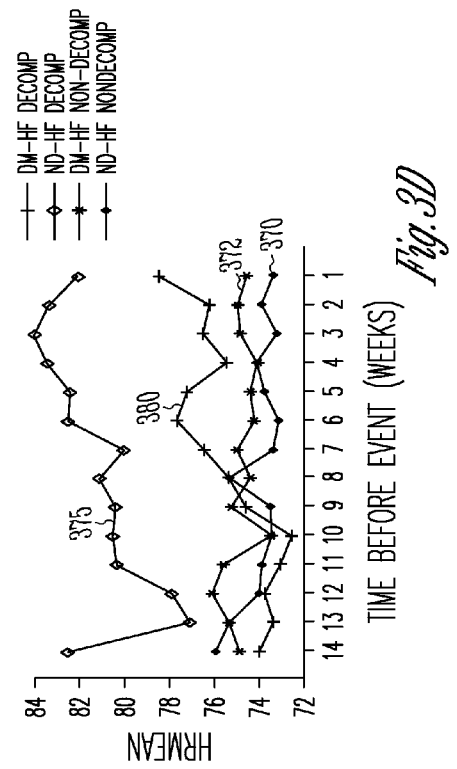

FIG. 3B shows graphs 325 of measurements of minimum heart rate (HRMin) versus time taken during a period before a HF decompensation event. Graph 330 includes HRMin for subjects that experienced HF, did not undergo decompensation during the period, and were non-diabetic. Graph 332 includes HRMin for subjects that experienced HF, did not undergo decompensation during the period, and were diabetic. Graph 335 includes HRMin for subjects that experienced HF, underwent decompensation, and are non-diabetic. Graph 340 includes HRMin for subjects that experienced HF, underwent decompensation, and were diabetic.

The graphs 325 show that HRMin increased during the period for subjects that underwent decompensation. The increase may be due to the decompensated heart trying to increase output. However, HRMin increased less for those subjects that underwent decompensation and had diabetes. The graphs 345 also show that the slopes of the change in HRMin during the period are different between subjects having a co-morbidity of diabetes and subjects that don't have diabetes.

Figure 3C:
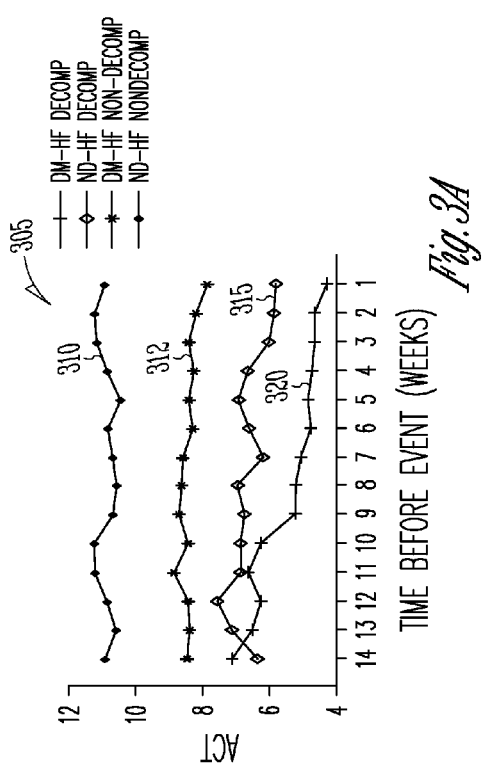

FIG. 3C shows graphs 345 of measurements of the standard deviation of sequential mean R-R intervals (SDANN) versus time taken during a period before a HF decompensation event. Graph 350 includes SDANN for subjects that experienced HF, did not undergo decompensation during the period, and were non-diabetic. Graph 352 includes SDANN for subjects that experienced HF, did not undergo decompensation during the period, and were diabetic. Graph 355 includes SDANN for subjects that experienced HF, underwent decompensation, and are non-diabetic. Graph 360 includes SDANN for subjects that experienced HF, underwent decompensation, and were diabetic. The graphs 345 show that a five percent change in SDANN may not be significant for a non-diabetic HF patient, but could be an indicator of a potential HF event in a HF patient with diabetes.

Figure 3D:
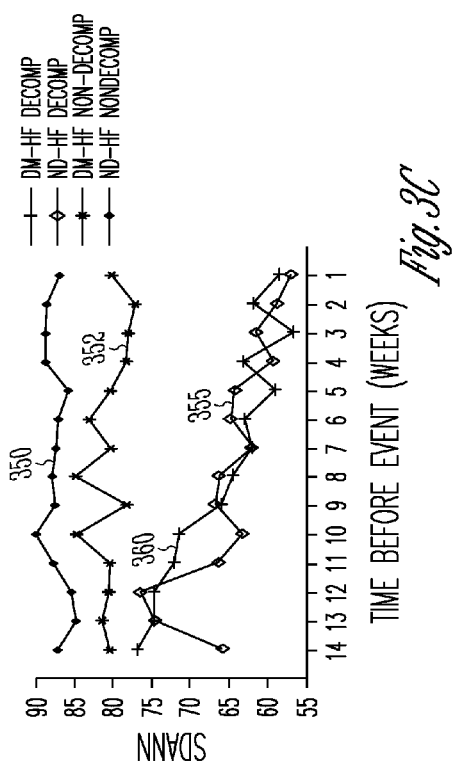

FIG. 3D shows graphs 365 of measurements of mean heart rate (HRMean) versus time taken during a period before a HF decompensation event. Graph 370 includes HRMean for subjects that experienced HF, did not undergo decompensation during the period, and were non-diabetic. Graph 332 includes HRMean for subjects that experienced HF, did not undergo decompensation during the period, and were diabetic. Graph 375 includes HRMean for subjects that experienced HF, underwent decompensation, and are non-diabetic. Graph 380 includes HRMean for subjects that experienced HF, underwent decompensation, and were diabetic. The graphs 365 show that HRMean increased during the period for subjects that underwent decompensation. Graph 380 shows that the HRMean increased less for those subjects that underwent decompensation and had diabetes. The graphs 365 also show that the slopes of the change in HRMean during the period are different between subjects having a co-morbidity of diabetes and subjects that don't have diabetes.

The example measurements in FIGS. 3A-3D show that measurements of hemodynamic parameters leading up to an event associated with HF may be different for individuals with co-morbidities (e.g., diabetes) than for individuals without co-morbidities, and may be different for patients with different combinations of co-morbidities. The examples also show that device-based diagnostics may be able to reflect the differences caused by co-morbidities if the devices are sensitive to those differences.

Figure 4:
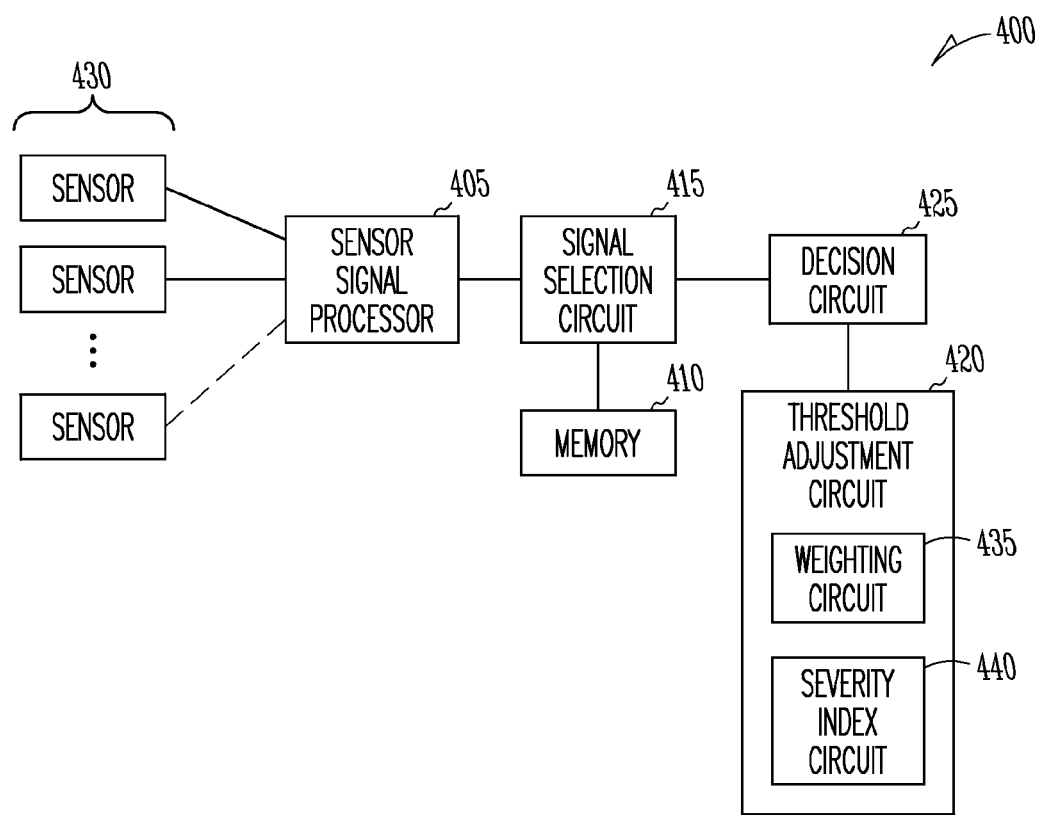
FIG. 4 is a block diagram of an example of a system to monitor one or more hemodynamic parameters of a subject.

FIG. 4 is a block diagram of an example of a system 400 to monitor one or more hemodynamic parameters of a subject. The system 400 includes a sensor signal processor 405, a memory 410, and a sensor signal selection circuit 415. The sensor signal processor 405 receives a plurality of electrical sensor signals produced by a plurality of sensors. The sensors may be in electrical communication with the sensor signal processor 405 by being integral to the system 400, electrically connected to the system, or remote from the system 400 and provide a sensor signal by a wireless communication method. At least one sensor signal is produced by an implantable sensor, such as a sensor included in an implantable medical device (IMD) for example.

The memory 410 includes information indicating a co-morbidity of the subject or patient. The sensor signal selection circuit 415 is in electrical communication with the sensor signal processor 405 and the memory 410. The sensor signal selection circuit 415 selects a sensor signal to monitor from among the plurality of sensor signals, according to an indicated co-morbidity.

For example, if the information indicates that the subject is a diabetic, the sensor signal selection circuit 415 optionally selects a glucose sensor signal to monitor. If the information indicates that the subject experiences apnea or hypopnea, the sensor signal selection circuit 415 optionally selects a respiration sensor signal indicative of respiration or breathing, such as from a respiration sensor or a pulse oximeter sensor. If the information indicates the patient has chronic-obstructive pulmonary disorder (COPD), sensor signal selection circuit 415 optionally selects an airflow sensor signal to monitor.

In some examples, selecting a sensor signal includes enabling the sensor producing the signal and/or enabling a sensor interface circuit. In some examples, if no co-morbidity is indicated, the sensor signal selection circuit 415 selects one or more default sensor signals to monitor and uses a default sensor detection threshold of the default sensor signal when no co-morbidity is indicated. A user is also able to select or remove sensor signals to monitor.

The sensor signal may be added to a default set of sensor signals when a co-morbidity is indicated. For example, monitoring the glucose sensor signal may be added to monitoring a cardiac depolarization produced by a cardiac signal sensor. In certain examples, the sensor signal selection circuit 415 selects a sensor signal to monitor according to an indicated co-morbidity in addition to sensors selected or programmed for monitoring by a physician.

The system 400 also includes a threshold adjustment circuit 420 and a decision circuit 425. The threshold adjustment circuit 420 adjusts a detection threshold of the selected sensor signal according to the indicated co-morbidity.

For example, the sensor signal processor 405 may receive an activity sensor signal from an activity sensor, such as an accelerometer. The activity sensor signal is representative of activity of the subject. The sensor signal processor 405 may use the activity sensor signal to monitor sensed activity of the subject in an activity log. As in FIG. 3A, if the activity log indicates that the activity of the subject decreases below a predetermined threshold level for a predetermined period of time, or the rate or slope of activity is decreasing faster than a predetermined rate, this may indicate a worsening condition of HF for the subject. If the co-morbidity information indicates a co-morbidity for the subject (e.g., diabetes), the threshold adjustment circuit 420 may vary the threshold level or rate such that the algorithm is more sensitive to small changes in activity.

Additionally, the memory 410 may include information indicating a cardiovascular condition of the subject. The threshold adjustment circuit 420 adjusts a detection threshold of the selected sensor signal according to the indicated cardiovascular condition.

For example, the sensor signal processor 405 may receive a cardiac signal representative of cardiac depolarizations of the subject. The sensor signal processor 405 monitors the minimum heart rate or a mean heart rate of the subject. If the minimum or mean heart rate increases above a predetermined threshold heart rate, or is increasing with a slope faster than a predetermined threshold slope, this may be an indication of a worsening condition of HF for the subject. If the co-morbidity information indicates a co-morbidity for the subject, the threshold adjustment circuit 420 may decrease the predetermined threshold heart rate or predetermined threshold heart rate slope to detect the indication of a worsening condition of HF. Optionally, the threshold adjustment circuit 420 may use the cardiovascular condition information (e.g., an indication that the subject is receiving cardiac resynchronization therapy (CRT)) to decrease the predetermined threshold heart rate to detect the indication. The threshold adjustment circuit 420 may also decrease the threshold using the co-morbidity information in conjunction with the cardiovascular condition information.

In accordance with HF detection criteria, the decision circuit 425 applies the adjusted detection threshold to the selected sensor signal to determine whether an event associated with worsening heart failure (HF) occurred in the subject. The decision circuit 425 outputs an indication of whether the event associated with worsening HF occurred to a user or process.

In some examples, the system 400 includes a plurality of sensors 430. Each sensor is configured to produce an electrical sensor signal that includes physiologic information of a subject. At least one of the sensors is an implantable sensor. The sensor signal selection circuit 415 may select a sensor signal according to an indicated co-morbidity. For example, the plurality of sensors 430 may include an activity sensor (e.g., an accelerometer) that produces the signal representative of activity of the subject describes previously. The sensor signal selection circuit 415 selects the activity signal to monitor according to an indicated co-morbidity (e.g., diabetes).

In some examples, the plurality of sensors 430 includes a cardiac signal sensor that produces a sensor signal representative of an intrinsic cardiac signal of the subject. An example of a cardiac signal sensor includes electrodes and sense amplifiers described in regard to FIG. 1. Another example of a cardiac signal sensing circuit is an ECG sensing circuit. The ECG sensing circuit may be an external device and may communicate with the system using a wired interface (e.g., Universal Serial Bus interface) or a wireless interface (e.g., radio frequency). Another example of a cardiac signal sensing circuit is a wireless ECG circuit. A wireless ECG circuit produces a signal approximating the surface ECG and is acquired without using surface (skin contact) electrodes. An example of a circuit for sensing the wireless ECG is discussed in commonly assigned, U.S. Patent Application Publication No. 20050197674, entitled "Wireless ECG in Implantable Devices," filed on Mar. 5, 2004, which is incorporated herein by reference in its entirety.

As described previously, the sensor signal processor 405 may receive the signal produced by the cardiac signal sensor to monitor heart rate. In another example, the sensor signal processor 405 may use the cardiac signal sensor to monitor heart rate variability (HRV). HRV refers to the variability of the time intervals between successive heart beats during a sinus rhythm. In some examples of the system 400, the first condition includes a detected decrease in HRV. A patient with a low amount of measured HRV implies that the patient may have a decreased ability to compensate for changes in arterial pressure. Systems and methods to measure HRV are described in Carlson et al., U.S. Pat. No. 7,248,919, entitled "Cardiac Rhythm Management System Using Time Domain Heart Rate Variability Indicia," filed Dec. 2, 2003, which is incorporated herein by reference in its entirety. If the co-morbidity information indicates a co-morbidity for the subject, the threshold adjustment circuit 420 may decrease a predetermined variability threshold to determine that an event associated with worsening HF occurred.

In yet another example, the sensor signal processor 405 may monitor HRV by measuring the SDANN of the subject. If the SDANN decreases below a predetermined threshold SDANN or is decreasing at a predetermined rate or slope, this may be an indication of a worsening condition of HF for the subject. If the co-morbidity information indicates a co-morbidity for the subject, the threshold adjustment circuit 420 may decrease the predetermined threshold SDANN or predetermined threshold SDANN slope to detect smaller changes that may be indicative of a worsening condition of HF.

In some examples, the plurality of sensors 430 includes a heart sound sensor. The heart sound sensor produces a heart sound signal representative of mechanical activity of the heart of the subject. Because ischemia is associated with a decrease in ventricular chamber contractility, ischemia is correlated to a decrease in the loudness of the S1 heart sound. In some examples, if the co-morbidity information indicates a co-morbidity for the subject (e.g., MI), the signal selection circuit 415 selects the heart sound sensor signal to monitor. A description of systems and methods for monitoring heart sounds is found in U.S. Patent Application Publication No. 20060282000, entitled "Ischemia Detection Using a Heart Sound Sensor," filed on Jun. 8, 2005, which is incorporated herein by reference in its entirety. In some examples, if the co-morbidity information indicates a co-morbidity for the subject, the threshold adjustment circuit 420 may lower the necessary threshold decrease in the sensor signal to detect the indication of a worsening condition of HF.

In certain examples, the decision circuit 425 may establish a baseline signal for a received sensor signal (e.g., a heart sound signal). The decision circuit 425 may determine that the event associated with worsening HF occurred when a change in a measurement derived from a sensor signal differs from an established measurement baseline value by more than a detection threshold change value. The threshold adjustment circuit 420 may decrease the detection threshold change value based on an indicated co-morbidity (e.g., MI).

In some examples, the plurality of sensors 430 includes a weight sensor. The sensor signal selection circuit 415 may select a weight sensor signal to monitor according to an indicated co-morbidity (e.g., diabetes). The threshold adjustment circuit 420 may decrease a necessary detection threshold change value according to the indicated co-morbidity.

In some examples, the plurality of sensors 430 includes a blood pressure sensor. In some examples, the blood pressure sensor is included in an external device, such as a sphygmomanometer or a finger-cuff sensor, in communication with the system 400. In some examples, the plurality of sensors 430 includes an implantable cardiac pressure sensor. An implantable cardiac pressure sensor can be used to measure chamber pressure of the left ventricle. In an example, a pressure sensor is implanted in a coronary vessel to determine left ventricle pressure by direct measurement of coronary vessel pressure. A description of systems and methods that use such an implantable pressure sensor is found in Salo et al., U.S. Pat. No. 6,666,826, entitled "METHOD AND APPARATUS FOR MEASURING LEFT VENTRICULAR PRESSURE," filed Jan. 4, 2002, which is incorporated herein by reference in its entirety. Other cardiac pressure sensors examples include a right ventricle (RV) chamber pressure sensor, a pulmonary artery pressure sensor, and a left atrial chamber pressure sensor. The sensor signal selection circuit 415 may select a weight sensor signal to monitor according to an indicated co-morbidity (e.g., hypertension, MI). The threshold adjustment circuit 420 may decrease a necessary detection threshold change value according to the indicated co-morbidity.

In some examples, the plurality of sensors 430 includes a respiration sensor to provide a signal representative of respiration of the subject. The respiration sensor produces a respiration signal, such as an electrical or optical respiration signal, that includes information about the respiration of the subject. In certain examples, the respiration sensor can include an implantable sensor including at least one of an accelerometer, an impedance sensor, and a pressure sensor. The respiration signal can include any signal indicative of the respiration of the subject, such as inspiration, expiration, or any combination, permutation, or component of the respiration of the subject. An example of an implantable respiration sensor is a transthoracic impedance sensor to measure minute respiration volume. An approach to measuring transthoracic impedance is described in Hartley et al., U.S. Pat. No. 6,076,015, "Rate Adaptive Cardiac Rhythm Management Device Using Transthoracic Impedance," filed Feb. 27, 1998, which is incorporated herein by reference in its entirety. In some examples, the plurality of sensors 430 includes an intra-thoracic impedance sensor (ITTI). The sensor signal selection circuit 415 may select a respiration signal to monitor according to an indicated co-morbidity (e.g., COPD, apnea). The threshold adjustment circuit 420 may decrease a necessary detection threshold change value according to the indicated co-morbidity.

In some examples, the system 400 includes a pulmonary arterial pressure (PAP) sensor. A signal produced by an implantable PAP sensor can be used to detect a reduction in blood supply to a portion of the heart. An approach for detecting a reduction in blood supply to a portion of the heart using PA pressure is described in Zhang et al., commonly assigned, co-pending, U.S. patent application Ser. No. 11/624,974, entitled "Ischemia Detection Using Pressure Sensor," filed Jan. 19, 2007, which is incorporated herein by reference in its entirety. The sensor signal selection circuit 415 may select a respiration signal to monitor according to an indicated co-morbidity (e.g., hypertension, MI). The threshold adjustment circuit 420 may decrease a necessary detection threshold change value according to the indicated co-morbidity.

In some examples, the system 400 includes a cardiac stroke volume sensor to produce a signal representative of the cardiac stroke volume of the subject. Examples of stroke volume sensing are discussed in Salo et al., U.S. Pat. No. 4,686,987, "Biomedical Method And Apparatus For Controlling The Administration Of Therapy To A Patient In Response To Changes In Physiologic Demand," filed Mar. 29, 1982, which is incorporated herein by reference in its entirety. If the co-morbidity information indicates a co-morbidity for the subject (e.g., hypertension, MI), the sensor signal selection circuit 415 may select a respiration signal to monitor according to an indicated co-morbidity (e.g., hypertension, MI). The threshold adjustment circuit 420 may decrease the signal feature threshold (e.g., amplitude) necessary to detect the indication of a worsening condition of HF according to the indicated co-morbidity.

In some examples, the system 400 includes an air flow sensor. An example of an air flow sensor includes an air flow sensor implantable into the trachea of the subject. Descriptions of implantable air flow sensors are found in Piaget et al., U.S. patent application Ser. No. 11/379,396, "Implanted Air Passage Sensor," filed on Apr. 20, 2006, which is incorporated herein by reference in its entirety. In some examples, the sensor signal selection circuit 415 selects to monitor an air flow sensor signal according to an indicated co-morbidity (e.g., COPD). The threshold adjustment circuit 420 may decrease the signal feature threshold necessary to detect the indication of a worsening condition of HF according to the indicated co-morbidity.

According to some examples, the memory 410 includes information indicating a severity of the co-morbidity. For example, the information may indicate that the subject's diabetes is mild, moderate, or severe. The sensor signal selection circuit 415 may use the co-morbidity and severity information to determine a combination of sensor signals to monitor. For example, if the information indicates that the subject has severe diabetes, the sensor signal selection circuit 415 may select to monitor both a signal produced by a glucose sensor that monitors a level of glucose in the subject's blood or interstitial fluid and an activity sensor signal. Other chemical sensors may be used to monitor other co-morbidities of the subject. An approach to providing a chemical sensor in a coronary sinus is found in Kane et al., U.S. patent application Ser. No. 11/383,933, entitled, "Implantable Medical Device with Chemical Sensor and Related Methods, filed May 17, 2006, which is incorporated herein by reference in its entirety.

In some examples, the threshold adjustment circuit 420 includes a weighting circuit 435 to weight physiologic information from a sensor signal according to the co-morbidity and severity information. The weighting may be based on the presence and/or the severity of certain co-morbidities or patient conditions and may be used to further adjust a detection threshold of the selected sensor signal. For example, the weighting circuit 435 may assign a low weight to an ITTI sensor and a high weight to an air flow sensor if the co-morbidity information includes an indication of COPD for the subject. Thus, the threshold adjustment circuit 420 may weight information from a first sensor signal differently than information from a second sensor signal using the co-morbidity and severity information. If the information includes an indication of severe COPD for the subject, the threshold adjustment circuit 420 may adjust the detection threshold to be more sensitive (e.g., a higher threshold of air flow) than if the subject had mild COPD. Thus, the threshold adjustment circuit 420 may use a rule based approach to adjust a detection threshold of the selected sensor signal according to the indicated co-morbidity and co-morbidity severity.

In some examples, the threshold adjustment circuit 420 includes a severity index circuit 440 that calculates a severity index for the subject using the co-morbidity and severity data.

TABLE 1

| Co-morbidity | No (0) | Mild (1) | Moderate (2) | Severe (3) |
|---|---|---|---|---|
| DM | | | x | |
| HTN | x | | | |
| Apnea | | x | | |
| MI | | | x | |
| COPD | x | | | |

Table 1 includes a list of example co-morbidities and indicates severity of the co-morbidity; from not having the co-morbidity (No) to having a severe case of the co-morbidity. The severity is provided a score. In the example, the score varies from 0 to 3. In some examples, the system includes a user interface (not shown). A table, such as Table 1, is filled in by a physician when enabling HF detection criteria in the system 400. In certain examples, the severity index circuit 440 calculates a total severity index I by summing all of the severity scores.

The severity index may be used by the threshold adjustment circuit 420 to adjust a detection threshold of one or more sensor signals. This is shown in Table 2. The higher the severity index, the more sensitive the threshold is adjusted by the threshold adjustment circuit 420.

TABLE 2

| Total severity index I | Adjust Sensor Threshold by |
|---|---|
| 1 | 10% |
| 2 | 20% |
| 3 | 30% |
| 4 | 40% |
| 5 | 50% |

For example, assume the co-morbidity information indicates the co-morbidities and severities of Table 1. The Total Severity Index for the subject is 5 and the threshold adjustment circuit 420 adjusts the detection threshold for a sensor by 50% to make the threshold more sensitive to detect events associated with HF. Further assume the system 400 includes a heart sound sensor, the decision circuit 425 establishes a baseline signal for the heart sound signal, and the decision circuit 425 uses a decrease in signal amplitude of the S1 heart sound to detect an event associated with HF. Because of the indicated co-morbidities and the severity index, the threshold adjustment circuit 420 would reduce the threshold necessary to alert for an impending HF event. The decision circuit 425 applies the adjusted threshold to the selected sensor signal to determine whether an HF event occurred. In certain examples, the threshold is applied to a composite signal obtained from multiple signals from the sensors. In certain examples, the threshold adjustment circuit 420 implements fuzzy logic rules to blend weighted sensor signals and severity indexes to arrive at an adjusted detection threshold.

In some examples, the weighting circuit 435 weights the information from a sensor signal according to the severity index. In the example of Table 2, because the subject has moderate MI and no indication of hypertension, the weighting circuit 435 may weight a sensor signal received from a heart sound sensor greater than a sensor signal received from a blood pressure sensor. The decision circuit 425 weights the signal from the heart sound signal greater when determining whether an HF event occurred. Thus, in some examples the system 400 is rule based, and the threshold adjustment circuit 420, in conjunction with the sensor signal selection circuit 415, uses a rule to adjust a detection threshold of the selected sensor signal according to an indicated co-morbidity.

Figure 5:
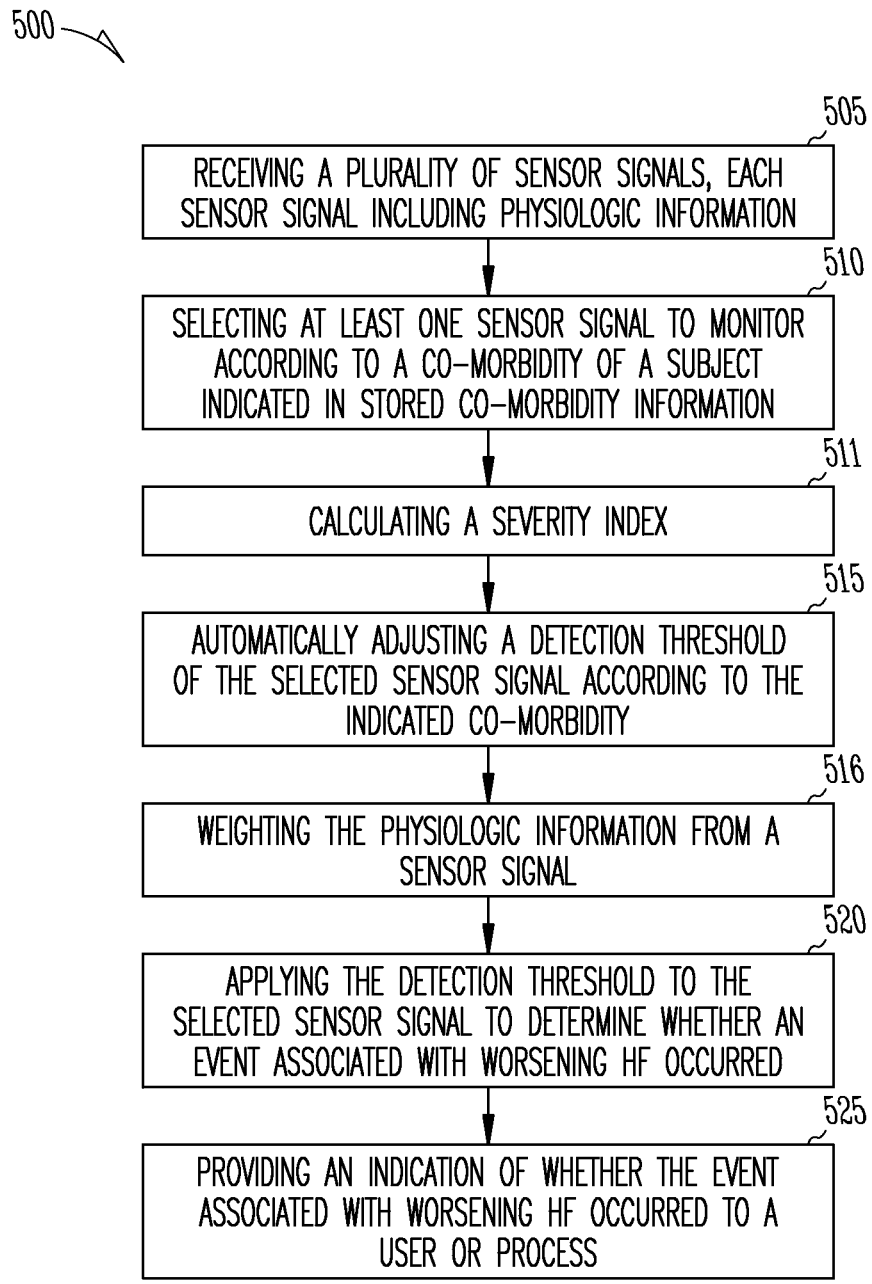
FIG. 5 is a flow diagram of an example of a method to monitor one or more hemodynamic parameters of a subject.

FIG. 5 is a flow diagram of an example of a method 500 to monitor one or more hemodynamic parameters of a subject. At block 505, a plurality of sensor signals is received. Each sensor signal includes physiologic information, and at least one of the sensor signals is provided by an implantable sensor.

At block 510, at least one sensor signal is selected to monitor according to a co-morbidity of a subject indicated in stored co-morbidity information. In some examples, the co-morbidity information is included in electronic medical records (EMR), and the data is accessed by a first device (e.g., a medical device programmer) from a second remote device (e.g., a server) via a communication network such as the internet or a cell phone network. In some examples, the co-morbidity information includes an indication of the severity of a co-morbidity and one or more sensor signals are selected using the co-morbidity and the severity information. In certain examples, the co-morbidity information is stored and/or changed periodically by a physician during patient follow up visits using the programmer or the remote device.

In some examples, selecting the sensor signal includes calculating a severity index at block 511. In certain examples, the stored information includes a cardiovascular condition of the subject and at least one sensor signal is selected to monitor according to the cardiovascular condition.

At block 515, a detection threshold of the selected sensor signal is automatically adjusted according to the indicated co-morbidity. In some examples, the detection threshold is adjusted using the severity index. In some examples, the physiologic information from a sensor signal is weighted according to the co-morbidity and the co-morbidity severity indicated in the stored co-morbidity information at block 516.

At block 520, the detection threshold is applied to the selected sensor signal to determine whether an event associated with worsening HF occurred. In some examples, a plurality of sensor signals is used to determine whether the HF event occurred. In some examples, the sensor signals (or the physiologic information represented by the sensor signals) are weighted, and whether the HF event occurred is determined using the weighted signals. At block 525, an indication is provided to a user or process of whether the event associated with worsening HF occurred. In some examples, the indication is displayed to a user on an external device. In some examples, the indication is communicated to a process from a first device to a second device.

Figure 6:
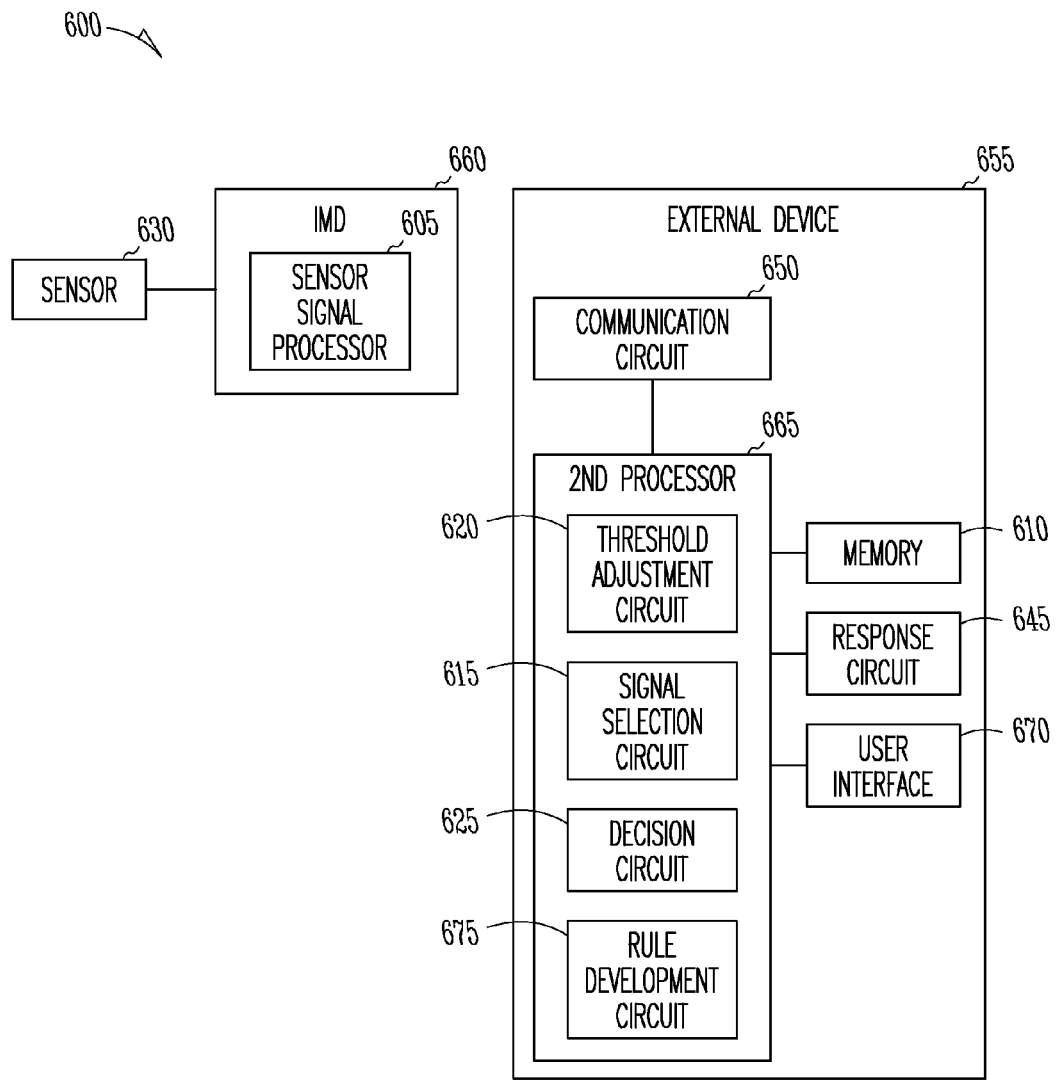
FIG. 6 is another block diagram of another example of a system to monitor one or more hemodynamic parameters of a subject.

FIG. 6 is another block diagram of another example of a system 600 to monitor one or more hemodynamic parameters of a subject. The system 600 includes an IMD 660. The IMD 660 includes a sensor signal processor 605 and is electrical communication with at least one sensor 630. The sensor 630 may be integral to the IMD 660, may be coupled to the IMD 660 via a lead or other wired connection, or may be a second IMD that communicates wirelessly with the first IMD 660. The sensor may provide any of the type of sensor signals described herein to the sensor signal processor 605.

The system 600 also includes an external device 655. The external device 655 includes a communication circuit 650 to communicate wirelessly with the IMD 660. In some examples, the external device 655 includes an IMD programmer. In some examples, the external device 655 includes a remote computer that is configured to communicate with the IMD over a network. In certain examples, the remote computer is a remote server that communicates with the IMD 660 via a third device, such as a repeater located near the subject for example.

The external device 655 also includes a memory 610 and a second processor 665. The memory includes information indicating a co-morbidity of a subject. In some examples, the memory 610 includes an indication of the severity of the co-morbidity and/or an indication of a cardiovascular condition of the subject.

The second processor 665 is in electrical communication with the communication circuit 650 and the memory 610, and includes a sensor signal selection circuit 615, a threshold adjustment circuit 620, and a decision circuit 625. The sensor signal selection circuit 615 selects a sensor signal to monitor from among a plurality of sensor signals, according a co-morbidity indicated in the memory 610. The threshold adjustment circuit 620 adjusts a detection threshold of the selected sensor signal according to the indicated co-morbidity. The decision circuit 625 applies the adjusted detection threshold to a selected sensor signal to determine whether an event associated with worsening HF occurred in the subject.

The external device 655 also includes a response circuit 645 in electrical communication with the second processor. The response circuit 645 provides a specified response when the event associated with worsening HF is declared. In some examples, the external device 655 includes a display in electrical communication with the response circuit 645, and the response circuit 645 displays an indication that an HF event occurred. In some examples, the response circuit 645 communicates the indication to another device, such as a remote server for example. In some examples, the response circuit initiates a therapy provided to the subject by the IMD 660 when an HF event occurs.

In some examples, the system 600 is rule based, and the threshold adjustment circuit 620, in conjunction with the sensor signal selection circuit 615, uses a rule to adjust a detection threshold of a selected sensor signal according to an indicated co-morbidity. In certain examples, the external device 655 includes a user interface 670 in electrical communication with the second processor 665. The user interface 670 may include a display and a device to receive user input, such as a keyboard, keypad, touch screen, or computer mouse.

The second processor 665 may include a rule development circuit 675. The rule development circuit 675 develops the rule used by the threshold adjustment circuit 620 to adjust the detection threshold of a sensor signal. In certain examples, a physician enters co-morbidity data through the user interface 670 such as by filling out a table like Table 1. In certain examples, the rule development circuit 675 includes a decision tree, such as a series of IF-THEN statements implemented in software or firmware for example. The rule development circuit 675 traverses the decision tree to arrive at an adjustment of the detection threshold.

In certain examples, the rule development circuit 675 allows a physician to create a customizable rule through the user interface 670. For example, the threshold adjustment circuit 620 may include a weighting circuit and/or a severity index circuit as described herein. The rule development circuit 675 may allow the physician to assign weights top sensor signals based on the physician's professional experience. In certain examples, the rule development circuit 675 allows the physician to assign detection thresholds to sensor signals according to a calculated severity index.

The external device 655 may also receive sensor signals from other external sensors. The external device may also use pre-recorded data received from sensors and apply an adjusted threshold to detect an HF event from the recorded data.

The different circuits described may be allocated differently between an IMD and an external device and still perform their indicated functions. To which device they are allocated would be a design-based decision based on factors that include cost, size of the IMD, and battery life of the IMD battery.

Figure 7:
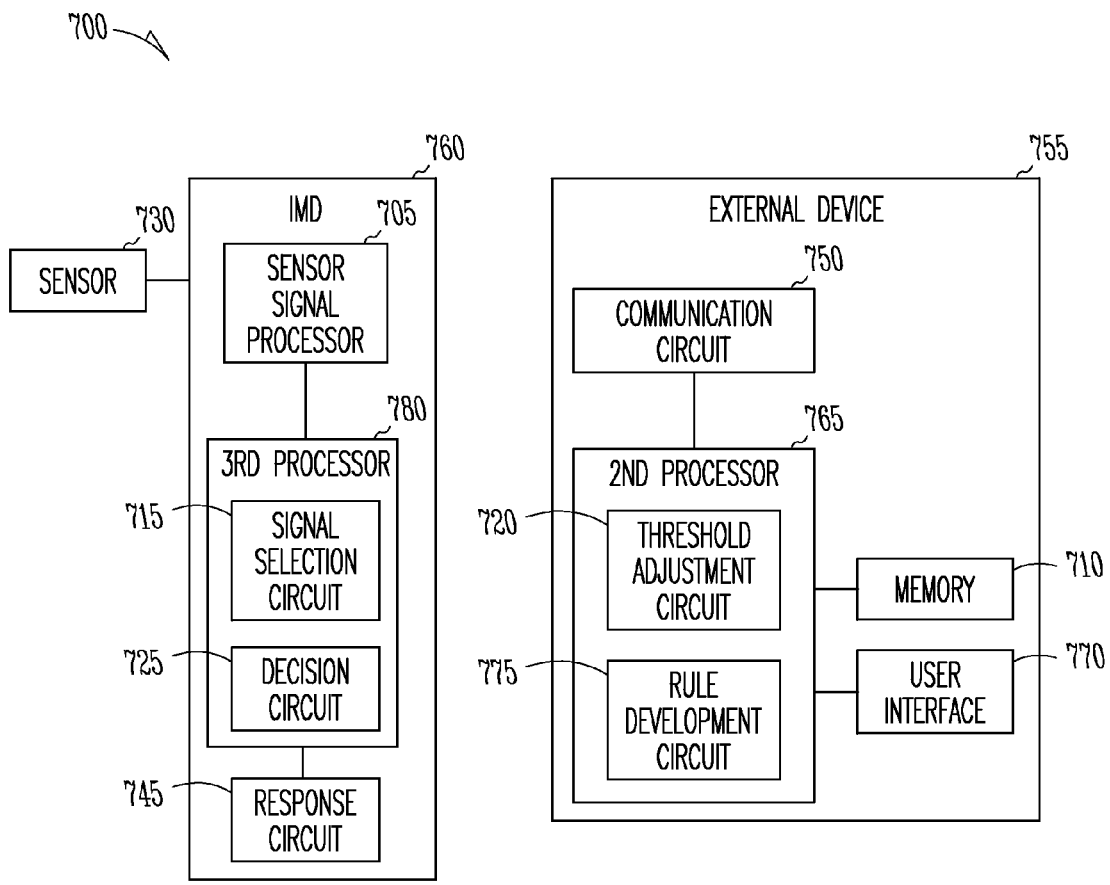
FIG. 7 is another block diagram of yet another example of a system to monitor one or more hemodynamic parameters of a subject.

FIG. 7 is another block diagram of yet another example of a system 700 to monitor one or more hemodynamic parameters of a subject. The system 700 includes an external device 755 and an IMD 760. The external device 755 includes a communication circuit 750 to communicate wirelessly with the IMD 760, a memory 710 that includes an indication of a co-morbidity of the subject, and a second processor 765. The second processor 765 includes a threshold adjustment circuit 720.

The IMD 760 includes a sensor signal processor 705 in electrical communication with at least one sensor 730. The IMD 760 also includes a third processor 780. The third processor 780 receives a sensor detection threshold from the threshold adjustment circuit 720 via the communication circuit 750. The third processor 780 includes a sensor signal selection circuit 715 and a decision circuit 725. The decision circuit 725 applies the received detection threshold to a sensor signal selected by the sensor signal selection circuit 715 to determine whether an event associated with worsening HF occurred in the subject. The IMD 760 further includes a response circuit 745 in electrical communication with the decision circuit 725 to provide a specified response when the event associated with worsening HF is declared.

In some examples, the external device 755 includes a user interface 770 in electrical communication with the second processor 765. The second processor 765 includes a rule development circuit 775 to develop a rule via the user interface 770. The threshold adjustment circuit 720, in conjunction with the sensor signal selection circuit 715, uses the rule to adjust a detection threshold of a selected sensor signal according to an indicated co-morbidity and to selectively weight information from the selected sensor signal.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
   a sensor signal processor configured to receive a first sensor signal produced using a first physiologic sensor and at least one second sensor signal produced using at least one second physiologic sensor;
   a memory configured to store information associated with co-morbidities of a subject;
   a sensor signal selection circuit configured to enable the at least one second physiologic sensor according to information associated with at least one co-morbidity of the subject; and
   a decision circuit configured to generate an indication of heart failure (HF) status of the subject according to the first sensor signal and the at least one second sensor signal.

2. The system of claim 1, including a threshold adjustment circuit configured to adjust a detection threshold of the first sensor signal as a function of the indicated co-morbidity, wherein the decision circuit is configured to generate the indication of HF status using the first sensor signal, an adjusted detection threshold of the first sensor signal, and the second sensor signal.

3. The system of claim 2, wherein the threshold adjustment circuit is configured to adjust a detection threshold of the at least one second sensor signal as a function of the indicated co-morbidity, wherein the decision circuit is configured to determine worsening of the HF condition of the subject using the first sensor signal, the at least one second sensor signal, and adjusted detection thresholds of the first sensor signal and the second sensor signal.

4. The system of claim 2, wherein the threshold adjustment circuit is configured to adjust a detection threshold of the first sensor signal as a function of a first indicated co-morbidity, and adjust a detection threshold of the at least one second sensor signal as a function of a second indicated co-morbidity.

5. The system of claim 1, wherein the sensor signal processor is configured to receive the first sensor signal and at least a second sensor signal and a third sensor signal, wherein the sensor signal selection circuit is configured to selectively enable sensing of one or both of the second sensor signal and the third sensor signal according to information associated with at the least one co-morbidity of the subject, and wherein the decision circuit is configured to generate the indication of HF status according to the first sensor signal and the selectively enabled one or both of the second sensor signal and the third sensor signal.

6. The system of claim 5, wherein the memory is configured to store co-morbidity severity information, wherein the threshold adjustment circuit includes a weighting circuit configured to change a weighting that a selectively enabled sensor signal is accorded in generating the indication of HF status based on co-morbidity severity information.

7. The system of claim 5, wherein the memory is configured to store co-morbidity severity information, wherein the system includes a severity index circuit configured to calculate a severity index for the subject using the co-morbidity severity information, and wherein sensor signal selection circuit is configured to selectively enable sensing of one or both of the second sensor signal and the third sensor signal according to the calculated severity index.

8. The system of claim 1, including a weighting circuit and wherein the decision circuit is configured to weight the first sensor signal greater than the at least one second sensor signal when generating the indication of HF status.

9. The system of claim 1, wherein the sensor signal selection circuit is configured to only monitor and use the first sensor signal when the information associated with co-morbidities of a subject indicates no co-morbidity.

10. The system of claim 1, wherein the sensor signal processor, the memory, the sensor signal selection circuit, and the decision circuit are included in an implantable medical device.

11. The system of claim 1, wherein the signal processor is determined in an implantable medical device and the memory, the sensor signal selection circuit, and the decision circuit are included in an external device, and wherein the external medical device is configured to communicate an indication of one or more selected sensor signals to monitor and to communicate an indication of an adjusted detection threshold one or more selected sensor signals to the implantable medical device.

12. A method of operating a medical device, the method comprising:
   receiving, by the medical device, a first sensor signal and at least one second sensor signal, wherein the first sensor signal is produced using a first physiologic sensor and the at least one second sensor signal is produced using at least one second physiologic sensor;
   storing information associated with co-morbidities of a subject;

selectively enabling the at least one second physiologic sensor according to information associated with at least one co-morbidity of the subject; and generating an indication of HF status of the subject using the first sensor signal and the at least one second sensor signal, and generating an indication of worsening HF according to the determination.

13. The method of claim 12, including adjusting a detection threshold of the first sensor signal as a function of the co-morbidity information, wherein the generating the indication of HF status includes generating the indication of HF status using the first sensor signal, an adjusted detection threshold of the first sensor signal, and the second sensor signal.

14. The method of claim 12, including adjusting a detection threshold of the at least one second sensor signal as a function of the co-morbidity information, wherein the generating the indication of HF status includes generating the indication of HF status using the first sensor signal, the at least one second sensor signal, and adjusted detection thresholds of the first sensor signal and the second sensor signal.

15. The method of claim 12, wherein receiving a first sensor signal and at least one second sensor signal includes receiving the first sensor signal and at least a second sensor signal and a third sensor signal, wherein the selectively enabling includes selectively enabling sensing of one or both of the second sensor signal and the third sensor signal as a function of the co-morbidity information, and wherein the generating the indication of HF status includes generating the indication of HF status according to the first sensor signal and the selectively enabled one or both of the second sensor signal and the third sensor signal.

16. The method of claim 15, wherein the generating the indication of HF status includes weighting the first sensor signal and the selectively enabled one or both of the second sensor signal and the third sensor signal to generate the indication of HF status, and changing a weighting that a selectively enabled sensor signal is accorded in the generating based on the co-morbidity information.

17. The method of claim 16, including storing co-morbidity severity information, calculating a severity index for the subject using the co-morbidity severity information, and wherein the selectively enabling includes selectively enabling sensing of one or both of the second sensor signal and the third sensor signal according to the calculated severity index.

18. A system comprising:
a sensor signal processor configured to receive a first sensor signal produced using a first physiologic sensor and at least one second sensor signal produced using at least one second physiologic sensor;
a memory configured to store co-morbidity information associated with co-morbidities of a subject;
a decision circuit configured to generate an indication of HF status of the subject using at least one of the first sensor signal and the at least one second sensor signal; and at least one of:
a sensor signal selection circuit configured to enable the at least one second physiologic sensor as a function of the co-morbidity information;
a threshold adjustment circuit configured to adjust a detection threshold of one or more of the first sensor signal and the at least one second sensor signal as a function of the co-morbidity information; or
a weighting circuit configured to change a weighting, as a function of the co-morbidity information, that the first sensor signal and the at least one second sensor signal is accorded in generating the indication of HF status.

19. The system of claim 18, wherein the first sensor includes a cardiac signal sensing circuit, and the at least one second sensor includes at least one of an activity sensor, a weight sensor, a blood pressure sensor, an intra-thoracic impedance sensor, a respiration sensor, a heart sound sensor, a pulmonary arterial pressure (PAP) sensor, an air flow sensor, or a cardiac stroke volume sensor.

20. The system of claim 18, including the threshold adjustment circuit, wherein the decision circuit is configured to determine whether the event associated with worsening HF occurred when a change in a measurement derived from the first sensor signal differs from an established measurement baseline value by more than a detection threshold change value, and wherein the threshold adjustment circuit is configured to decrease the detection threshold change value based on the co-morbidity information.

* * * * *